United States Patent
Whayne et al.

(10) Patent No.: US 7,931,578 B2
(45) Date of Patent: Apr. 26, 2011

(54) METHODS AND SYSTEM FOR TISSUE CAVITY CLOSURE

(75) Inventors: James G. Whayne, Chapel Hill, NC (US); Sidney D. Fleischman, Durham, NC (US)

(73) Assignee: nContact Surgical, Inc., Morrisville, NC (US)

( * ) Notice: Subject to any disclaimer, the term of this patent is extended or adjusted under 35 U.S.C. 154(b) by 904 days.

(21) Appl. No.: 11/155,338

(22) Filed: Jun. 17, 2005

(65) Prior Publication Data

US 2006/0020162 A1    Jan. 26, 2006

Related U.S. Application Data

(60) Provisional application No. 60/580,890, filed on Jun. 18, 2004.

(51) Int. Cl.
*A61N 1/362* (2006.01)
(52) U.S. Cl. .......................................................... 600/16
(58) Field of Classification Search .................. 606/108, 606/130, 191, 232, 184, 138, 158, 213, 233, 606/139, 144, 153, 151; 600/16
See application file for complete search history.

(56) References Cited

U.S. PATENT DOCUMENTS

| | | | |
|---|---|---|---|
| 4,390,019 A | 6/1983 | LeVeen et al. | |
| 4,898,155 A * | 2/1990 | Ovil et al. | 606/144 |
| 4,924,864 A | 5/1990 | Danzig | |
| 5,125,928 A | 6/1992 | Parins et al. | |
| 5,219,359 A * | 6/1993 | McQuilkin et al. | 606/232 |
| 5,306,234 A | 4/1994 | Johnson | |
| 5,620,452 A | 4/1997 | Yoon | |
| 5,865,791 A | 2/1999 | Whayne et al. | |
| 6,132,438 A | 10/2000 | Fleischman et al. | |
| 6,152,144 A | 11/2000 | Lesh et al. | |
| 6,190,408 B1 * | 2/2001 | Melvin | 623/3.1 |
| 6,231,561 B1 | 5/2001 | Frazier et al. | |
| 6,419,669 B1 | 7/2002 | Frazier et al. | |
| 6,626,920 B2 * | 9/2003 | Whayne | 606/153 |
| 6,652,555 B1 | 11/2003 | VanTassel et al. | |
| 6,689,150 B1 | 2/2004 | VanTassel et al. | |
| 6,730,108 B2 | 5/2004 | Van Tassel et al. | |
| 6,986,774 B2 * | 1/2006 | Middleman et al. | 606/113 |
| 7,387,627 B2 | 6/2008 | Erb et al. | |
| 2003/0018358 A1 | 1/2003 | Saadat | |
| 2003/0078465 A1 | 4/2003 | Pai et al. | |
| 2006/0004388 A1 | 1/2006 | Whayne et al. | |

OTHER PUBLICATIONS

U.S. Appl. No. 11/155,305, filed Jun. 17, 2005 in the name of Whayne et al., Final Office Action mailed Aug. 13, 2009.
U.S. Appl. No. 11/155,305, filed Jun. 17, 2005 in the name of Whayne et al., Non-final Office Action mailed Oct. 28, 2008.
U.S. Appl. No. 11/155,305, filed Jun. 17, 2005 in the name of Whayne et al., Non-final Office Action mailed Oct. 13, 2010.

\* cited by examiner

*Primary Examiner* — George Manuel
*Assistant Examiner* — Robert N Wieland
(74) *Attorney, Agent, or Firm* — Levine Bagade Han LLP

(57) ABSTRACT

Surgical systems for less invasive access to and isolation of an atrial appendage are provided. A suturing grasper compresses soft tissue structures and deploys one or more sutures through complimentary pledget(s) carried by the grasper. The pledgets are reinforced, containing support members that define the profile of the stitch and distribute stresses applied by the stitch, once tightened, over a length of tissue. This hardware may be applicable to other surgical and catheter based applications as well including: compressing soft tissue structures lung resections and volume reductions; gastric procedures associated with reduction in volume, aneurysm repair, vessel ligation, or other procedure involving isolation of, resection of, and reduction of anatomic structures.

30 Claims, 12 Drawing Sheets

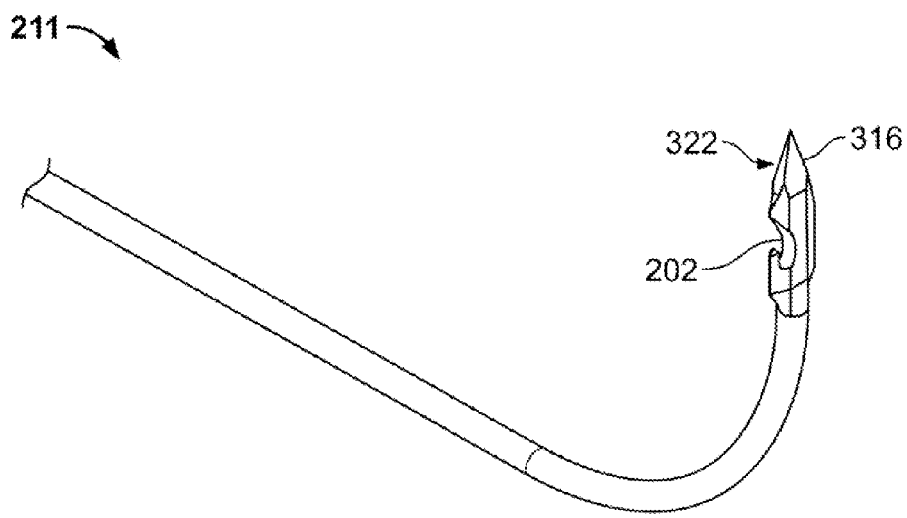
FIG. 8A
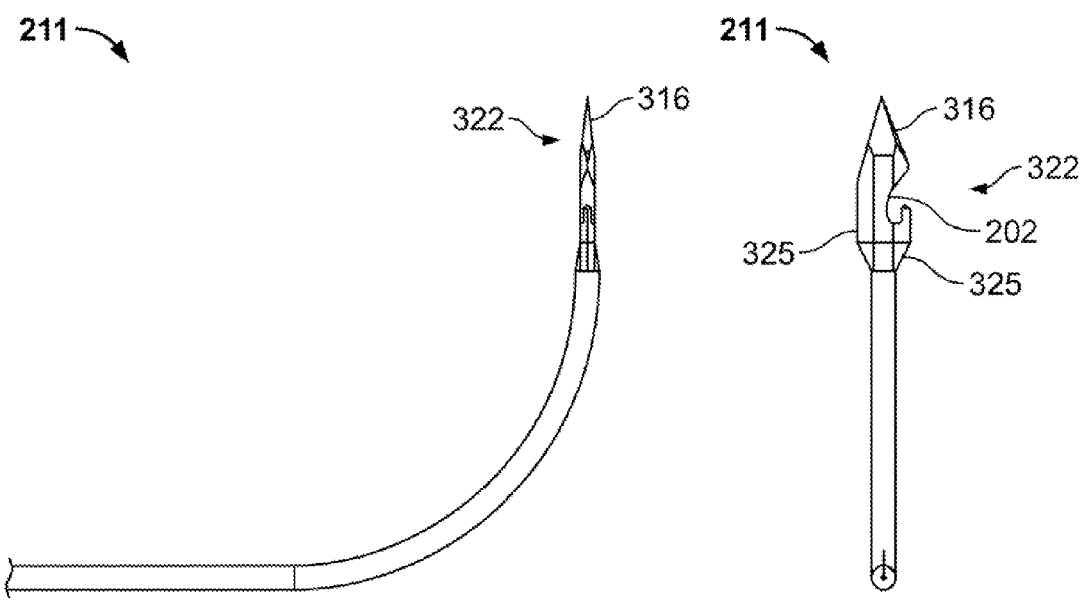
FIG. 8B  FIG. 8C

METHODS AND SYSTEM FOR TISSUE CAVITY CLOSURE

RELATED APPLICATION

This application is a non-provisional of U.S. Provisional Application No. 60/580,890 filed Jun. 18, 2004, the entirety of which is incorporated by reference.

FIELD OF THE INVENTION

This invention relates to devices and methods for less invasive treatment of atrial fibrillation or other application involving placing a pledgeted mattress suture stitch(es) to compress opposing tissue or to prevent its expansion.

BACKGROUND OF THE INVENTION

Surgical atrial fibrillation treatment involves eliminating the electrical propagation wavelets that trigger and sustain atrial fibrillation, and mitigating the risk of stroke by reducing the volume of enlarged the atria through isolation or resection of the atrial appendages. A previous surgical technique for resecting an atrial appendage involves manually advancing a suture, via an attached, curved, fixed needle, through the atrial appendage. This approach is performed under direct visualization during open heart surgery involving a media sternotomy or lateral thoracostomy. To advance the suture through tissue, the surgeon clamps the solid suture needle with a needle driver clamp and rotates the needle via twisting of the needle driver until the needle and attached suture are advanced through the soft tissue. Once the needle punctures through the soft tissue, the surgeon uses a forcep or the needle driver to grab the distal end of the needle and pull the suture through the puncture site. Once tightened, the suture or sutures employed bear down on the opposing tissue walls of the atrial apendage, thereby closing it off or isolating its interior from the remaining blood pool of the heart.

This technique is adequate when the patient is on cardiopulmonary bypass support and access to the heart is not restricted by the opening into the thoracic cavity, characteristic of a median sternotomy and long lateral thoracotomies. However, during beating heart procedures and minimally invasive access to the heart commonly associated with mini-sternotomies, mini-thoracotomies, port access, and subxiphoid access, such manual surgical techniques require too much time, are accompanied with significant bleeding, and are not able to adequately create the desired suture stitch to completely close the orifice into the atrial appendage.

Less invasive approaches, surgical and catheter-based have been identified to isolate the atrial appendage by a variety of techniques and methodologies. One such approach, as described in U.S. Pat. No. 5,306,234 entitled "Method for closing an atrial appendage", involves delivering multiple staples through an endoscopic stapler that clamps the atrial appendage and delivers staples between opposite tissue layers to compress the layers together. The stapling approach, however successful, causes abrasion and trauma between the metallic staple and the soft tissue surface. In addition, spacing of the staples determines whether the appendage is completely isolated.

Catheter-based approaches, such as those described in U.S. Pat. No. 6,730,108 entitled "Barrier device for ostium of left atrial appendage", U.S. Pat. No. 6,689,150 entitled "Filter apparatus for ostium of left atrial appendage", U.S. Pat. No. 6,652,555 entitled "Barrier device for covering the ostium of left atrial appendage", U.S. Pat. No. 6,152,144 entitled "Method and device for left atrial appendage occlusion", U.S. Pat. No. 6,231,561 entitled "Method and apparatus for closing a body lumen", and U.S. Pat. No. 6,419,669 entitled "Method and apparatus for patching a tissue opening", describe patches that are positioned at the opening into the atrial appendage to prevent blood and/or clots residing in the atrial appendage from escaping into the blood pool. These approaches leave foreign material exposed to blood flow which material increases the risk of thromboembolism and increases the possibility that patients undergoing this procedure still require anticoagulation regimen such as Coumadin to prevent clots from forming in the heart. In addition, the risk of dislodgement for such patches is high, whether associated with fracture of the patch attachment means, degradation of the patch materials, mechanical damage to the device during manual compression of the heart (e.g. CPR) or other unexpected mechanical manipulation. Any dislodgement of such patch-type devices is life-threatening.

Other approaches such as taught by U.S. Pat. No. 5,865,791 entitled, "Atrial appendage stasis reduction procedure and devices", U.S. Pat. No. 6,132,438 entitled, "Devices for installing stasis reducing means in body tissue", describe devices and techniques that place a tie around the atrial appendage and close the opening by tightening the tie into a small diameter loop, or by inserting anchors into tissue separated around the circumference of the opening such that once tightened, the diameter of the opening is decreased until the appendage is isolated from blood flow. These approaches either do not adequately attach the isolation device to the tissue surface or are associated with high stresses at the attachment point, which can lead to tissue abrasion, tearing, or other unwanted tissue response. The latter observation is also true in regard to the simple emplacement of sutures through the opposing atrial appendage walls to close-off the structure, where at the place where the sutures turn they can cut into the tissue.

U.S. patent application Publication No. 2003/0078465 addresses this problem with regard to mattress sutures employed for supporting or reshaping the heart muscle for treatment of congestive heart failure. However, this invention does not teach modes of treatment that are applicable specifically to atrial appendage isolation in terms of placing a pledgeted mattress suture stitch(es) to compress opposing tissue or to prevent its expansion.

As such there exists a need for the present invention in connection with addressing the various deficiencies of known atrial appendage isolation modes as well as extending the applicability of mattress suture applications as applicable to supporting, closing or reshaping tissue cavity regions such as in reduction or isolation of orifices or anatomic cavities such as lung reductions or resections, gastric reductions, and other soft tissue manipulation procedures. As such, the present invention offers a significant advance in the art.

SUMMARY OF THE INVENTION

Embodiments of the invention relate to devices and methods for less invasive treatment of atrial fibrillation or other application involving placing a pledgeted mattress suture stitch to compress opposing tissue together or prevent tissue expansion. More particularly, certain embodiments of the invention relate to appendage isolation suturing devices that enable reducing the volume of the atria, or isolating the atrial appendage to prevent clots from forming in the cavity and dislodging into an embolus capable of causing a thromboembolic event (e.g. stroke, myocardial infarction, pulmonary embolus, peripheral embolus). Furthermore the invention offers a means of improving hemodynamics during atrial fibrillation treatment procedures by virtue of its efficient operation avoidance of a requirement for bypass support.

Aspects of the invention also enable appendage isolation procedures to be performed less invasively through limited incisions that previously required large, open incisions with inherent morbidity and risks to other anatomic structures. The appendage isolation suture devices according to the present invention are capable of altering the geometry of an atrial appendage (or other soft tissue structure), via a median sternotomy, lateral thoracotomy, intercostals port-access, mini-sternotomy, other less invasive approaches involving subxiphoid access, inguinal approaches, or sub-thoracic approaches adjacent the diaphragm. It should be noted that, thought the disclosure makes reference to sutures, the devices herein may be affixed with other fastening devices and/or fastening means. Such devices and/or means being readily understood by those skilled in the art. Alternatively, the appendage isolation suturing devices according to the present invention can be modified for catheter-based applications by reconfiguring the device, and incorporating other feature tailored for intravascular access. As such, the inventive devices and methods may enable patients to undergo therapeutic surgical procedures while enduring less pain, expedited hospital stays, and shorter rehabilitative and recovery times.

To facilitate such activity, surgical systems according to the present invention are used to create a reinforced stitch that distributes forces along a length of compressed soft tissue surfaces. The surgical systems comprise a suturing grasper that compresses soft tissue structures and deploys suture through reinforced pledgets, housed by the grasper, and the soft tissue. The reinforced pledgets contain support members that define the profile of the stitch and distribute stresses applied by the tightened stitch over a length of tissue, as opposed to conventional suture knots and non-reinforced pledgeted suture knots that apply high stresses to localized puncture sites.

In the present invention, methods and devices are provided in which one or more deformable or resilient needles, and suture (one, two, or multiple strands) are passed through the atrial appendage (or other tissue) during a less invasive procedures. It should also be noted that the needles described herein may be standard needles that are attached to sutures. Furthermore, the invention contemplates sutures having stiffened ends which effectively function as needles. To accomplish this, the subject devices advance or retract needles (deformable or superelastic) such that they can be compressed into small lumens incorporated in a grasper having a small cross-sectional profile to facilitate utility during less invasive access procedures. Use of the needles enable advancing or retracting suture material through the atrial appendage and creating pledgeted stitches that distribute the stresses exerted by the stitch against the treated soft tissue.

In forming these subject product structures, one or more suture strands is advanced (sequentially or simultaneously) through the atrial appendage at a single location or multiple strategically distributed locations. The reinforced pledgets employed direct the compression of the treated anatomical structure to distribute the stresses applied by the stitches along a larger tissue surface. As such, the embodiments of the invention provide isolation devices capable of creating pledgeted stitches that increase reliability of the stitch, distribute the applied forces over a much greater length of soft tissue, and—in the case of performing an atrial appendage isolation procedure—ensure consistent closure of the appendage orifice. Embodiments of the invention also enable contacting and penetrating the atrial appendage, for creating pledgeted stitches capable of isolating the atrial appendage (or closing any other anatomic cavity), during less invasive access to anatomic regions where exposure is compromised by the confined space or difficult to reach anatomic surface.

When using superelastic needles in the subject (e.g., appendage isolation) devices, the needles are deflected into a straightened, low profile when compressed into a tubular constraint and return towards their preformed, resting, curved shape upon removal of the compressive forces. Alternatively, the needles are fabricated of malleable material such that they can be deformed from the straight, low profile configuration (for passing through a confining tube) into a curved or bent configuration by forcing the needle against a curved guide member incorporated in the appendage isolation device.

Nevertheless, it should be appreciated that the devices described herein can be applicable for use in other indications involving devices that are used to create a reinforced pledgeted stitch through soft tissue where access to the tissue is limited by a small opening into the cavity, confined space at the soft tissue interface, difficult to reach locations, or other anatomic limitation. The embodiments of the invention can be configured for the human anatomy; however, it should be noted that the embodiments of the invention can, in some cases, be tailored to other species, such as horses, by changing the geometry and sizes of the structures. Features of the invention also enable creating reinforced pledgeted stitches through the stomach for gastric reduction procedures, and through the lung lobes for lung reduction or resection procedures.

In sum, the present invention includes systems comprising any of the features described herein. Methodology, especially in connection with atrial appendage isolation also forms part of the invention. Further details associated with such a procedure are provided below. The invention is, however, directed towards or applicable to compressing soft tissue structures for a variety of applications including lung resections and volume reductions; gastric procedures associated with reduction in volume, aneurysm repair, vessel ligation, or other procedure involving isolation of, resection of, and reduction of anatomic structures. In regard to such procedures, those with skill in the art will easily appreciate the applicability of the present invention as well as grasp such details as omitted herefrom that are applicable in practicing the subject procedures.

Systems related to the present invention are discussed in SYSTEMS FOR TISSUE CAVITY CLOSURE filed Jun. 17, 2005 Ser. No. 11/155,305, the entirety of which is incorporated by reference herein.

BRIEF DESCRIPTION OF THE DRAWINGS

Each of the figures diagrammatically illustrates aspects of the invention. Of these:

FIGS. 8A to 8C show a perspective view, a side view, and an end view of the suture passer component of the appendage isolation grasper embodiment in a deployed orientation;

Variation of the invention from that shown in the figures is contemplated. The figures and following detailed description are provided merely for illustrative purposes of selected non-limiting examples of the present invention. This subject matter is not to be taken in a limiting sense, but is made merely for the purpose of explaining certain general principles of the inventions.

DETAILED DESCRIPTION

The following description focuses on the atrial appendage isolation aspect of the present invention. In this regard, a description of the subject methodology is first presented, then additional constructional details regarding a system adapted to accomplish the subject procedure. Finally, component materials and processing as may be used to achieve the desired component performance are disclosed.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Terms such as proximal, distal, near and far, are given meaning relative to the point of the operator. For example, the distal/far descriptions connote structures or portions of the device that are farther from the operator of the device. While, the proximal/near descriptions connote structures or portions of the device that are closer to the operator of the device.

Appendage Isolation Procedure

During less invasive procedures a trocar or introducer is inserted into the thoracic cavity. Access can be attained through an intercostal incision during a mini-thoracotomy or thoracostomy, a sub-xiphoid puncture, a mini-sternotomy incision, or other method to create an opening into the thoracic cavity. The pericardium is then opened by creating an initial incision into the pericardium and opening the incision to expose a heart 91, and primarily a left atrial appendage 97. When the right atrial appendage is targeted, the pericardium incision will be lengthened to expose a right atrial appendage 139.

Figure 1:
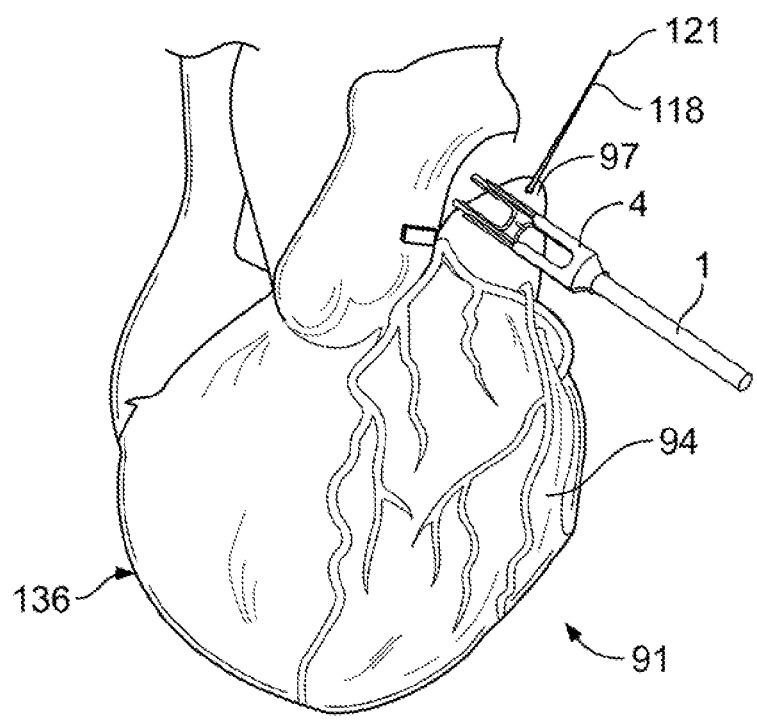
FIG. 1 shows a side view of a heart with the left atrial appendage engaged with the appendage isolation grasper embodiment of the invention.
Figure 2:
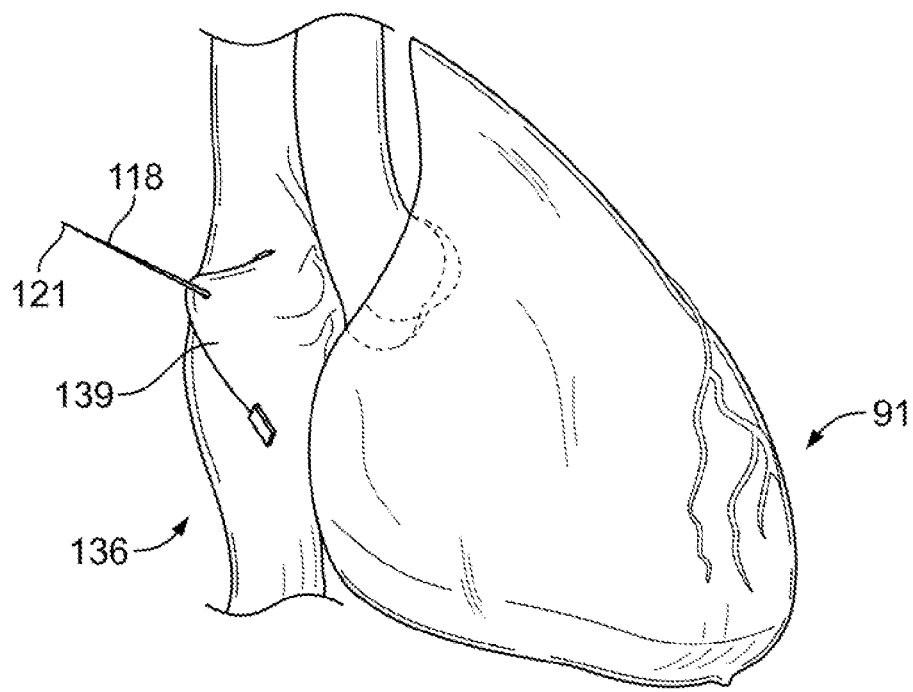
FIG. 2 shows a side view of a heart with the right atrial appendage pulled away from the right atrium.

As shown in FIG. 1, an appendage isolation grasper 1 is used to clamp a section of left atrial appendage 97 and bring the opposing atrial walls together. Alternatively, as shown in FIG. 2, right atrial appendage 139 can be targeted. A clamp 4 is positioned near the orifice of the atrial appendage (right or left) to ensure the maximum reduction in volume of the atrium (right 136 or left 94) and the isolation of the trabeculated, enlarged appendage without compromising apposition of the valve leaflets (tricuspid or mitral). As will be discussed below, appendage isolation device 1 houses a first reinforced pledget 109 on the lower jaw and a second reinforced pledget on a upper jaw 208 such that once needles 211 are actuated, deployed suture strand free end(s) 121 are passed through the first reinforced pledget, juxtaposed atrial appendage walls, and the second reinforced pledget. This ensures that, once tied, the stresses placed on the atrial appendage are distributed over a length of soft tissue, as opposed to conventional approaches where point forces are applied at suture penetration sites. Prior to a tying pledgeted stitch 112, the suture strand free ends can be brought outside a cannulae or introducer, and the suture strands are tied into a knot. Alternatively, a locking member can be advanced over the suture strand free ends to tighten a knot and prevent slipping of tightened suture strands 118. Multiple suture strands can be utilized during a single reinforced pledgeted stitch and can be interconnected or otherwise aligned to increase the tensile strength of the stitch.

Figure 3:
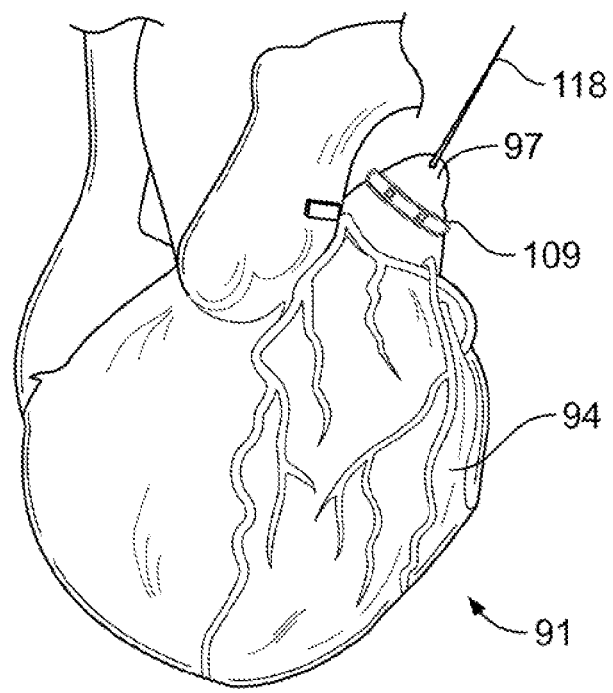
FIG. 3 shows a side view of a heart with the left atrial appendage isolated from blood flow by the appendage isolation pledgeted stitch embodiment of the invention.

FIG. 3 shows a side view of heart 91 that contains pledgeted stitch 109 isolating left atrial appendage 97 by juxtaposing opposing endocardial walls of left atrium 94 between two reinforced pledgets 109 such that clots within and the trabeculated interior surface of the left atrial appendage is separated from blood flow. In addition, left atrial volume is significantly reduced. Each suture strand 118 extends from outside the first reinforced pledget where continuous length of strand 115 defines an anchor, through an opening or puncture site in the first reinforced pledget, through the juxtaposed atrial walls, through an opening or puncture site in the second reinforced pledget, and outside the second reinforced pledget where suture strand free ends are tied into a knot or otherwise anchored to prevent relaxation of tightened stitch 112. Once the stitch is tightened, the reinforced pledgets are positioned intimately against the epicardial surfaces of the left atrial appendage and define the cross-sectional shape of the compressed atrial appendage. In embodiment 109 shown in FIG. 3, the reinforced pledgets are planar such that a flattened profile of the atrial appendage is maintained. This profile distributes the stresses applied to the soft tissue of the atrial appendage over the entire length of the reinforced pledget stitch. Alternatively, the reinforced pledget can incorporate a curved side section (e.g. profile).

Figure 4:
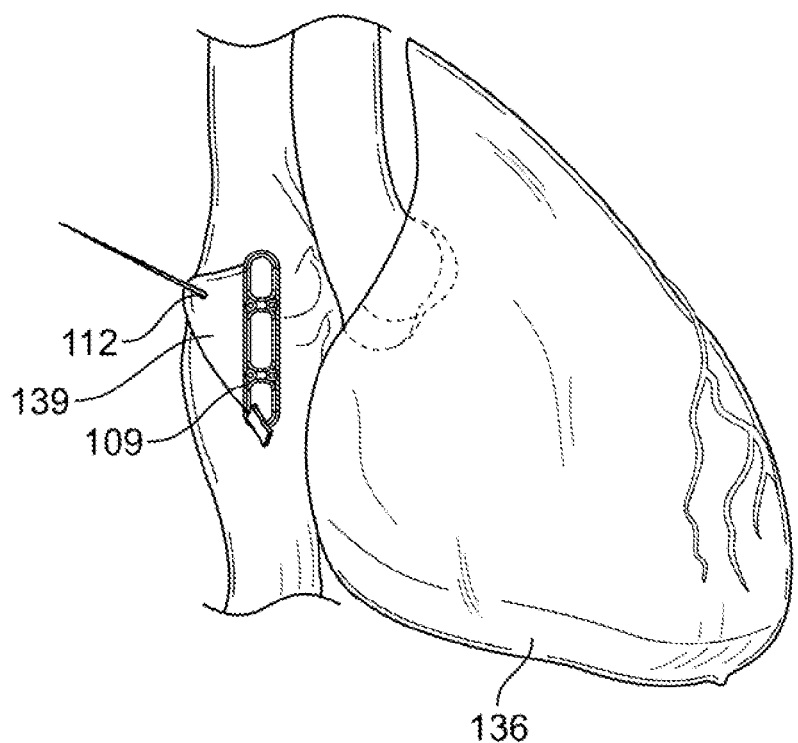
FIG. 4 shows a side view of a heart with the right atrial appendage isolated from blood flow by the appendage isolation pledgeted stitch embodiment of the invention.

FIG. 4 shows a side view of heart 1 that contains pledgeted stitch 112 isolating the right atrial appendage 139 by juxtaposing opposing endocardial walls of a right atrium 136 between two reinforced pledgets 109 positioned against the epicardial surfaces of the right atrium. As with isolating left atrial appendage 97, the reinforced pledgeted stitch comprises at least one suture strand 118 extending from outside the first reinforced pledget where the continuous length of strand defines an anchor, through an opening or puncture site in the first reinforced pledget, through the juxtaposed atrial walls, through an opening or puncture site in the second reinforced pledget, and outside the second reinforced pledget where suture strand free ends are tied into a knot or otherwise anchored to prevent relaxation of the tightened stitch.

Appendage Isolation System

Figure 5A:
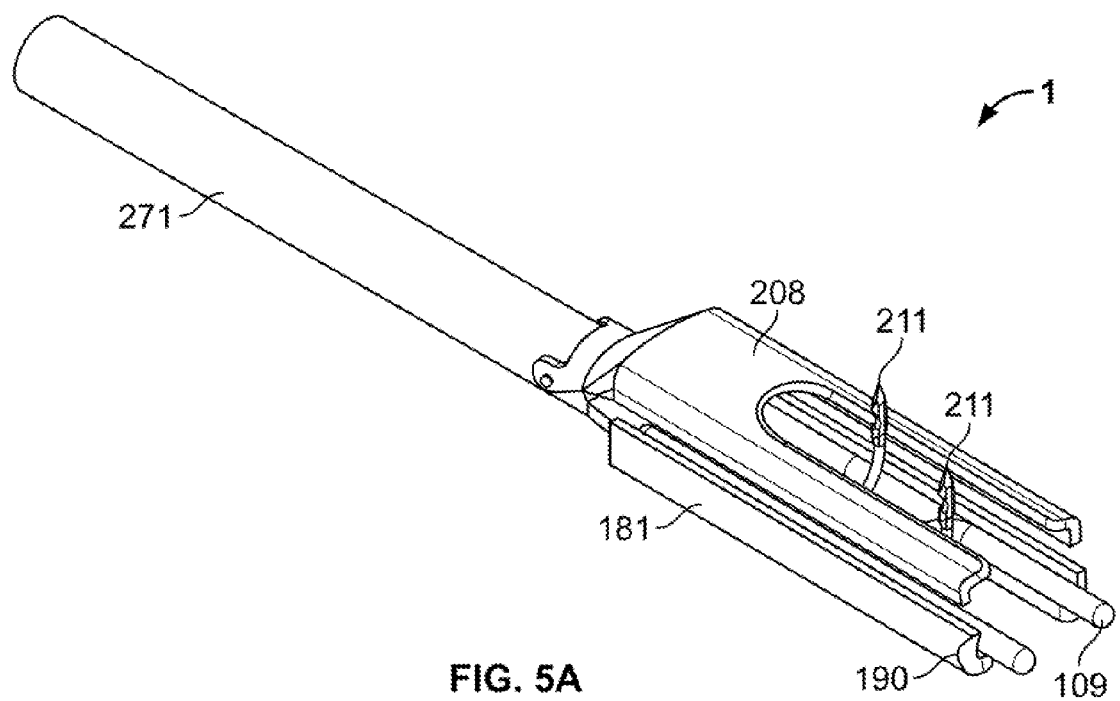
FIGS. 5A to 5D show a perspective view, a side view, and two end views of an appendage isolation grasper and associated pledget embodiment of the invention.
Figure 5B:
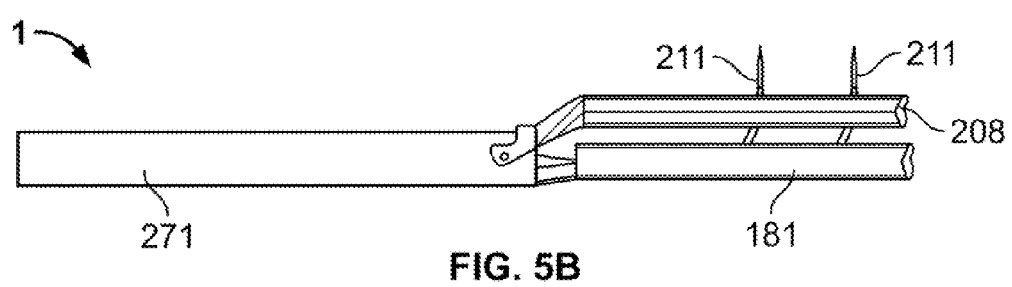
Figure 5C:
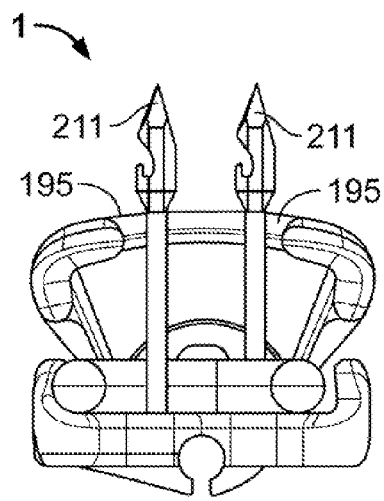
Figure 5D:
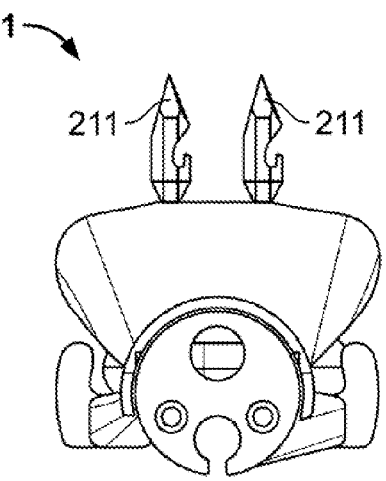
Figure 6A:
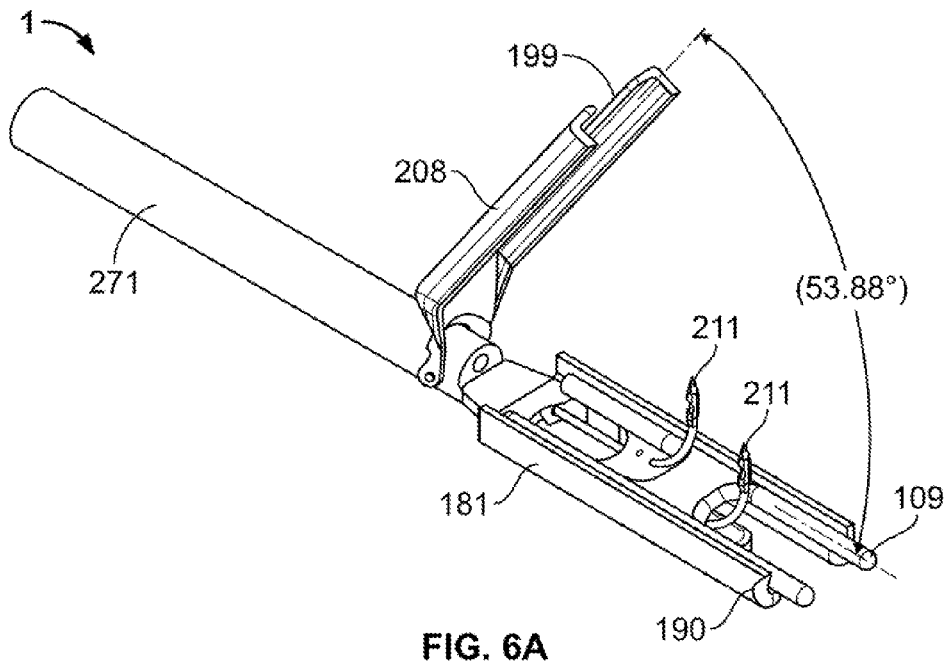
FIGS. 6A to 6C show a perspective view, a side view, and a top view of the appendage isolation grasper and associated pledget embodiment with the upper jaw in an opened orientation.
Figure 6B:
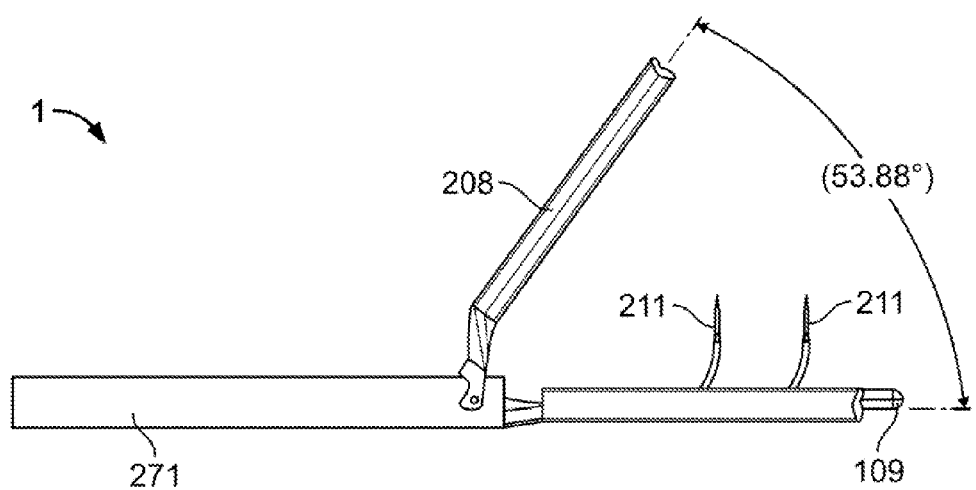
Figure 6C:
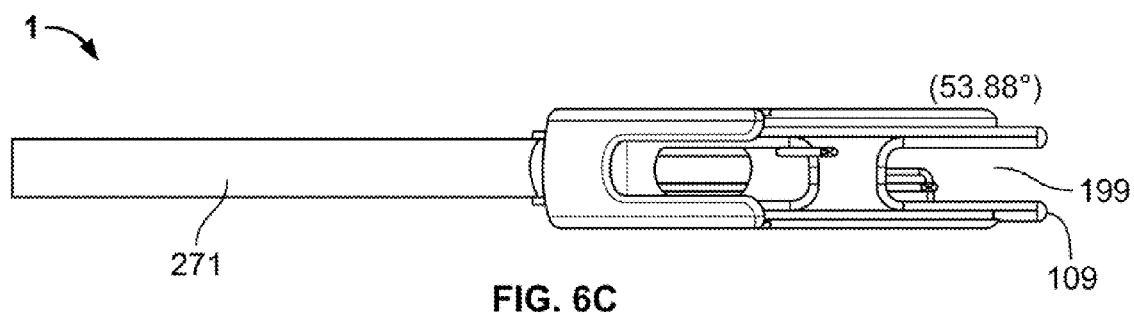

In embodiment 1 in FIGS. 5A to 5D and FIGS. 6A to 6C, appendage isolation grasper 1 is shown with single reinforced pledget 109 housed in lower jaw 181 (upper jaw 208 does not show a reinforced pledget purely for illustration purposes; in practice the upper jaw may or may not contain a reinforced pledget, depending on the application), and two resilient (or deformable) needles 211. FIGS. 5A to 5D show the grasper with the jaws in a closed orientation and with two resilient (or deformable) needles fully deployed. FIGS. 6A to 6C show the grasper with the upper jaw in an open orientation.

Appendage isolation grasper 1 incorporates two lumens into which the needles are compressed into a low profile for insertion through trocar, cannulae, or introducer. Lower jaw 181 incorporates two separate channels 190 associated with confining lumens and containing exit points 195 through which needles 211 pass. The lower jaw channels are curved to guide/direct the needles upward through reinforcing pledget 109 housed by the lower jaw, past clamped soft tissue structures, through the second reinforcing pledget (not shown) housed by the upper jaw, and beyond the upper jaw from where free ends 121 can be tied into a knot or anchored in a tightened configuration. The exit points are separated by an axial distance, Xsep, and a lateral distance Ysep that are specified according to the application, mechanical requirements of the grasper, and properties of the anatomy. At least one of Xsep and Ysep must be greater than 5 mm for isolating the atrial appendage and preferably one is greater than 10 mm.

For example, when clamping is to be axially aligned, such as when isolating atrial appendage 97 by clamping parallel to an orifice, Xsep is greater than 5 mm (preferably greater than 10 mm) and Ysep depends on the orientation of the channel lumens and the material properties; if the channels are oriented with one on top of the other, then Ysep is zero and a Zsep oriented perpendicular to the X-Y plane has a non-zero value. Otherwise Ysep is greater than maximum channel lumen diameter.

When clamping perpendicular to an orifice, Ysep is greater than 5 mm (preferably greater than 10 mm) and Xsep depends on the orientation of channel lumens 190 and the material properties, as remarked above. When clamping at a 45 degree angle to the orifice, Xsep equals Ysep and the square root of the sum of the squares (i.e. the hypotenuse) is greater than 5 mm and preferably greater than 10 mm.

Upper jaw 208 defines an open area 199 for needles 211, and accompanying suture 118, to pass. The needles are advanced enough through the upper jaw, as shown in FIGS. 5A to 5C to pass the suture strand fully through the opening of the upper jaw. Once an eyelet 202 containing the suture strand (s) is passed through reinforced pledgets 109 and clamped soft tissue (e.g. atrial appendage 97 or 139), the suture is grabbed with a separate forceps or other mechanism and is pulled through the cannulae to facilitate tying the free ends of the suture strands or anchoring into a tightened orientation with a separate locking mechanism (not shown). The appendage isolation grasper is then withdrawn through trocar, cannulae, or introducer leaving reinforced pledgeted stitch 112 around the compressed, isolated atrial appendage.

An embodiment 1 shown in FIGS. 5A to 5D and FIGS. 6A to 6C incorporates two needles 211 aligned axially therefore, both suture strands free ends 121 can be advanced through reinforced pledget 109 and soft tissue (e.g. atrial appendage 97 or 139) simultaneously. However, if appendage isolation system 1 only incorporates a single needle, then the steps above can be repeated for positioning each suture strand free end to enable creating reinforced pledgeted stitch 112.

Figure 7A:
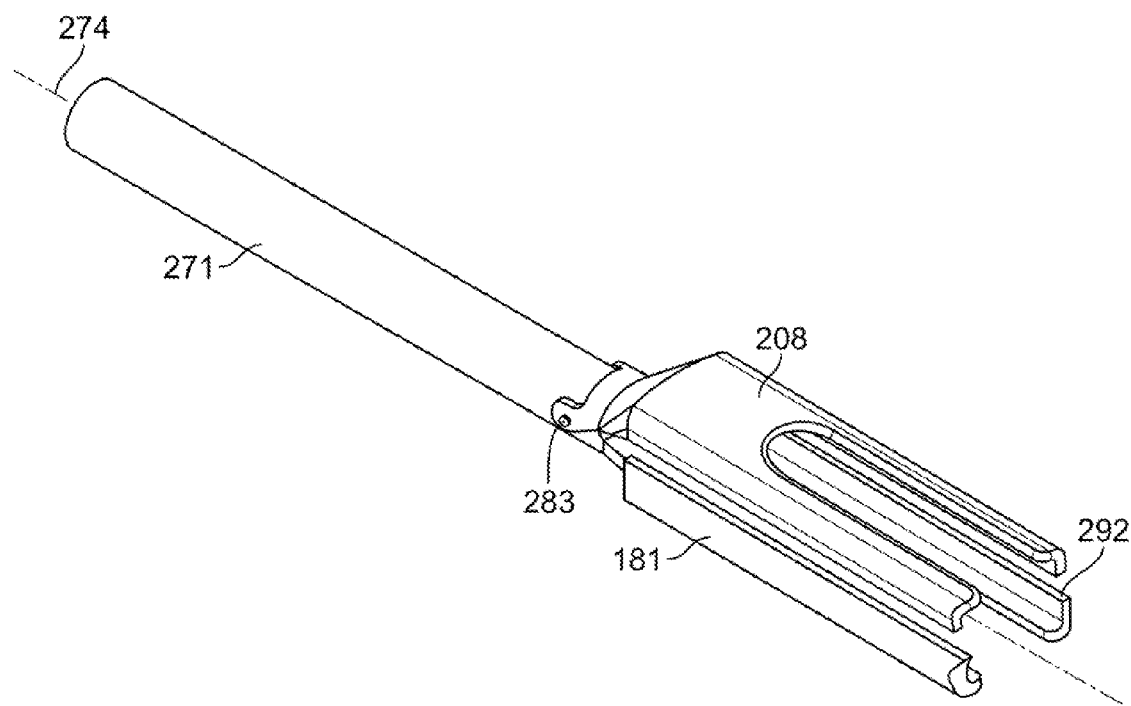
FIGS. 7A and B show a perspective view and a side view of the appendage isolation grasper embodiment with the upper jaw in a closed orientation.
Figure 7B:
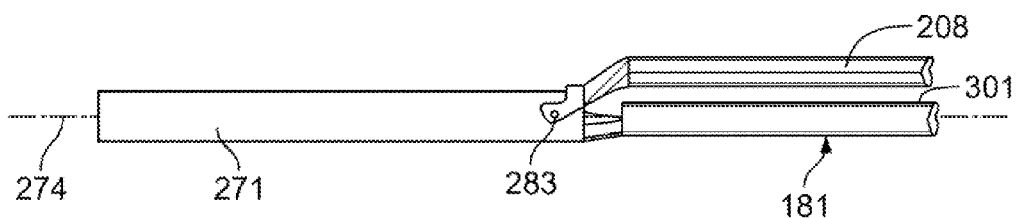

FIG. 7A and 7B show a perspective view and a side view of appendage isolation grasper 1 with jaws 181 and 208 closed. In this embodiment, the lower jaw is fixed to a shaft 271 of the grasper to define fixed channels/lumens 190 through which the needles traverse. The lower jaw incorporates a curved distal profile 292 in a channels adjacent exit point 193 to the lumen that parallels a grasper shaft axis 274. Curved distal channel ends 295 provide a surface off which the needles deflect, whether the needles are malleable or resilient. Incorporating curved ends also aids in compressing the needles into a low profile by gradually straightening as opposed to abruptly bending the needles. In addition, the curved channel profile better mimics the motion of rotating a needle through soft tissue. Finally, the curved channel profile prevents slipping of the needle into a gap 301 between the upper and lower jaw.

Upper jaw 208 pivots relative to shaft 271 and lower jaw 181 to enable opening the upper jaw to position around the anatomic surface and closing to clamp the anatomic structure in a compressed orientation. A stylet 277 connects to the upper jaw and is routed to an actuation knob (not shown) in the shaft 271. Pins 283 pivotably connect the upper jaw to the lower jaw or shaft to enable rotation of the upper jaw relative to the lower jaw and the upper jaw to the stylet to enable rotation of the stylet relative to the upper jaw during movement of the upper jaw as the stylet is actuated. A handle mechanism used to actuate the stylet, thus the upper jaw, and/or the superelastic puncturing components 211, can be a scissors type handle characteristic of a Rongeur device, a locking or non-locking forceps type handle characteristic of Castro Viejo Drivers, or other mechanism capable of independently or simultaneously actuating these components. If the handle mechanism is intended to simultaneously actuate the stylet and the needles, predetermined delays in the actuation of these components can be achieved by incorporating axial slots that the handle mechanism passes links through and springs that determine the engagement location of the links to the components. These approaches and similar type mechanisms permit actuating the upper jaw prior to advancing the needles and maintain clamping pressure on the soft tissue (e.g. atrial appendage 97 or 139) as the needles are advanced through the soft tissue. The mechanism reverses as the handle is released by retracting the needles prior to releasing the soft tissue with the upper jaw.

FIGS. 8A to 8C show a resilient or malleable needle 211 used with appendage isolation grasper 1 to advance or retract suture strand free ends. The needle incorporates a flattened distal end 316 (oriented parallel or perpendicular to a axis of the grasper) with eyelet 202 created along one (or both) sides 325 of a needle tip 322. The distal tip is beveled and sharpened to create a cutting tip capable of penetrating through the soft tissue (e.g. atrial appendage 97 or 139).

Figure 9A:
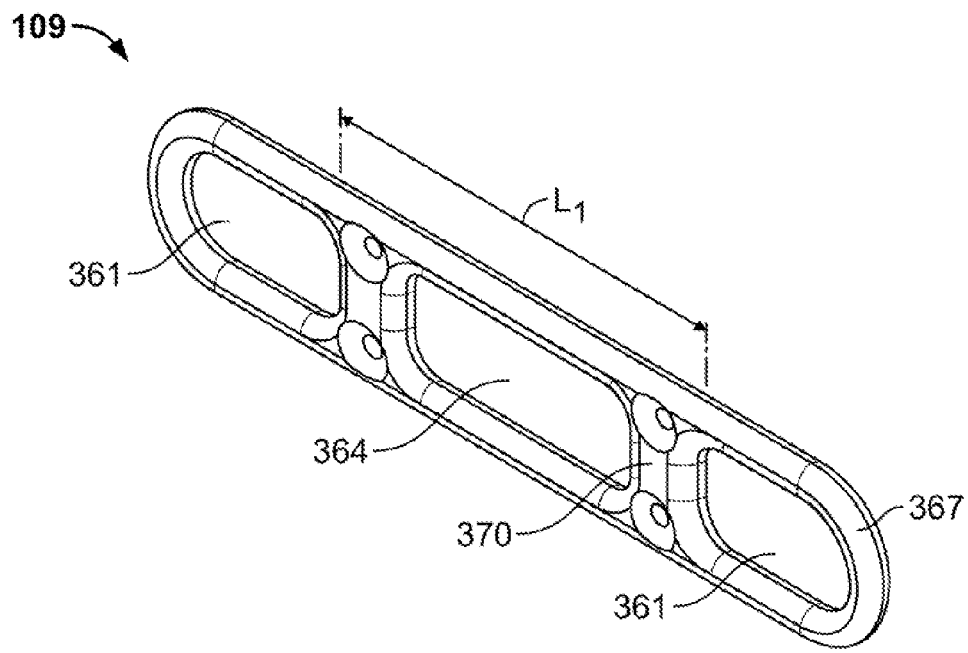
FIGS. 9A to 9C show a perspective view, a top view, and a side view of a reinforced pledget embodiment that contains a support structure to distribute the stresses exerted by the stitch.
Figure 9B:
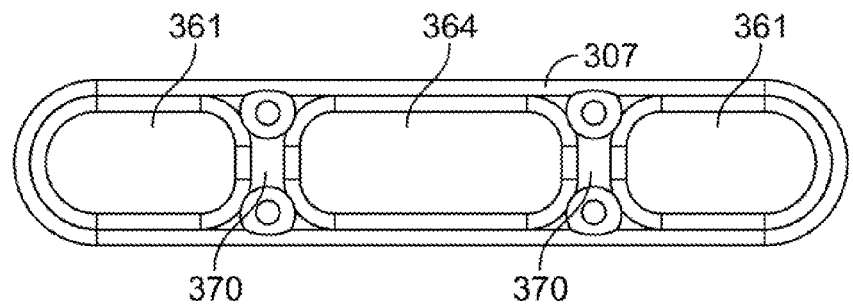
Figure 9C:
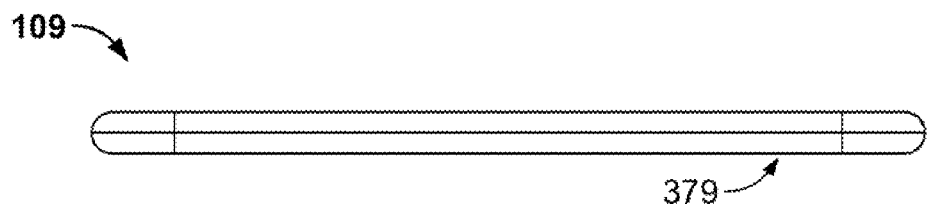

FIGS. 9A to 9C show a perspective view, a top view and a side view of reinforced pledget embodiment 109. This reinforced pledget embodiment incorporates three openings 361 and 364 in a support structure 367 through which suture strand free ends 121 are advanced using actuated needles 211 of appendage isolation system 1. The openings through the support structure are spaced to accommodate channel exit point 193 spacing for the grasper 1. The axial length ("$l_1$") of central opening 364 including the adjacent links 370 is chosen based on the stress distribution requirements and the size of soft tissue structure. As the flattened profile requirements are increased, the chosen length of the central link 370 is increased to accommodate the desire to distribute the forces along a greater length.

In general, the dimension of $I_1$ is chosen to accommodate the properties of the tissue on which the pledget is placed. For example, in cases where the pledget is placed over the atrial appendage, because of the friable and delicate nature of the tissue involved, the stress distribution should occur distances greater than approximately 2 mm. At distances of 2 mm or less, the tissue may not hold fasteners and sutures. However, to accommodate the varying geometry of the appendage, the maximum length of the stress distribution area should be approximately 7 mm. For example, better results may occur with two pledgets having $I_1$ spacing of 7 mm rather than a single pledget having spacing of 14 mm. In the latter case, the single larger pledget may not properly seat against the atrial tissue because of its varying geometry. Two smaller pledgets may better accommodate the varying geometry. In view of the above, while the spacing of the stress relief (and suture or faster spacing) may be between 3 and 7 mm for an atrial appendage application, the spacing may incorporate other ranges depending upon the application.

A covering (not shown) encapsulates the support structure to provide a compressible surface against soft tissue. Alternatively, the covering is not incorporated or the covering encapsulates only a portion of the support structure of is attached to one section of the support structure.

A profile 379 for embodiment 109 shown in FIG. 9C is planar to match the flattened profile of compressed atrial appendage 97 or 139. For other applications or for atrial appendages that have a more cylindrical orifice, the profile of the reinforced pledget can be curved into an arc, sinusoid, or other pattern capable of matching the inherent compressed geometry of the anatomy.

Figure 10A:
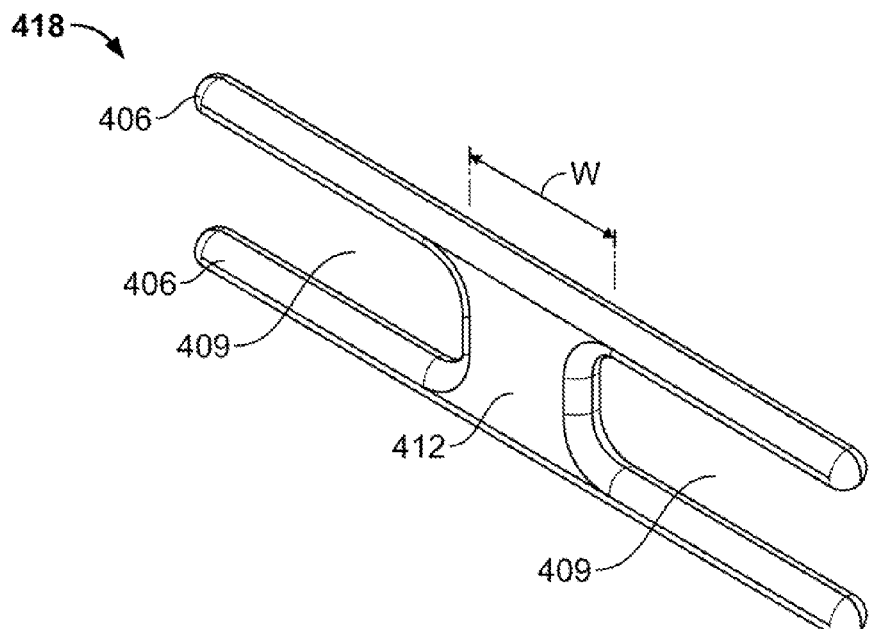
FIGS. 10A to 10C show a perspective view, a top view, and a side view of an alternative reinforced pledget embodiment.
Figure 10B:
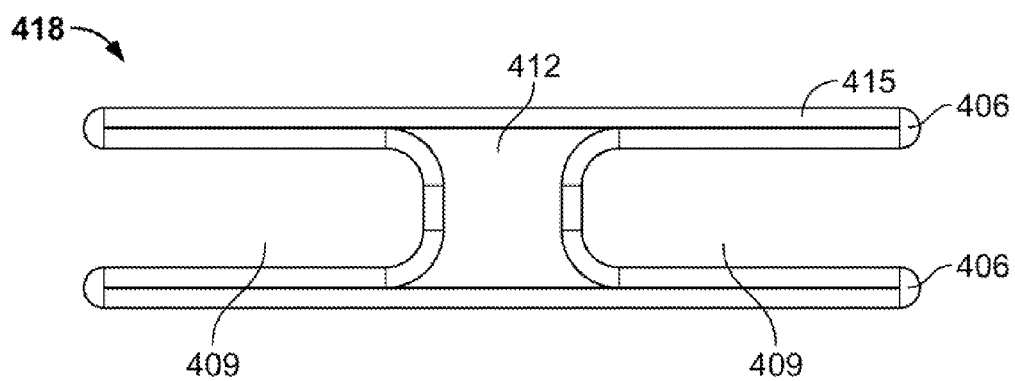
Figure 10C:
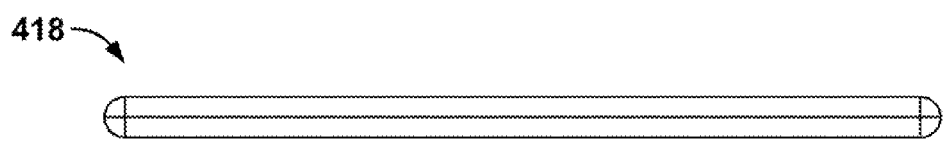

FIGS. 10A to 10C show a perspective view, a top view and a side view of another reinforced pledget embodiment 418. This reinforced pledget embodiment incorporates two openings 409 separated by a perpendicular central link 412 (having a width ("w") oriented axially to the reinforced pledget) and defining lateral barriers 406 in a support structure 415 through which suture strand free ends 121 are advanced using actuated needles 211 of appendage isolation system 1. The width of the central link is chosen based on the distribution requirements. For soft tissue structures (e.g. atrial appendages 97 or 139) whose flattened profile is wide, the width of the central link is increased to accommodate the desire to distribute the forces along a greater length. The openings through the support structure match channel exit point spacing 93 for the grasper. Ranges for the width are selected based on the application of the pledget (see the above discussion.) For example, for an atrial appendage application, w may range from between 3 and 7 mm.

Figure 11A:
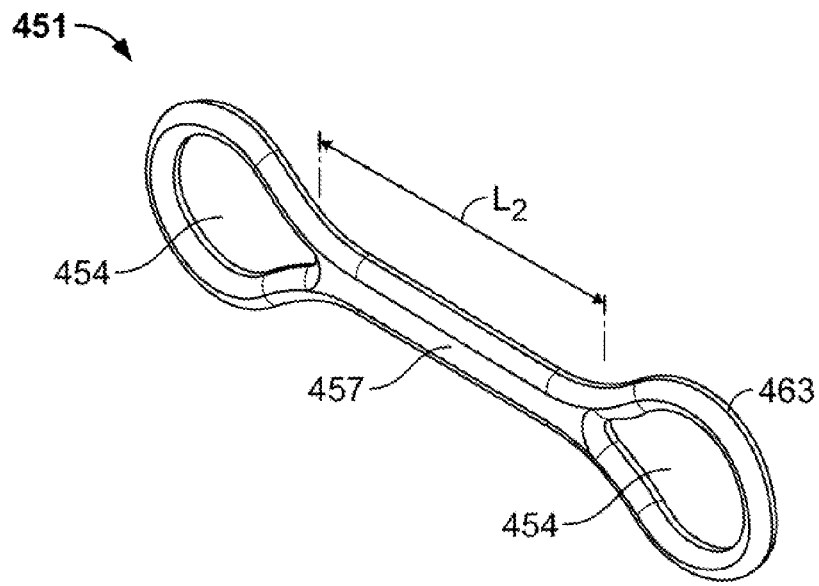
FIGS. 11A to 11C show a perspective view, a top view, and a side view of another reinforced pledget embodiment.
Figure 11B:
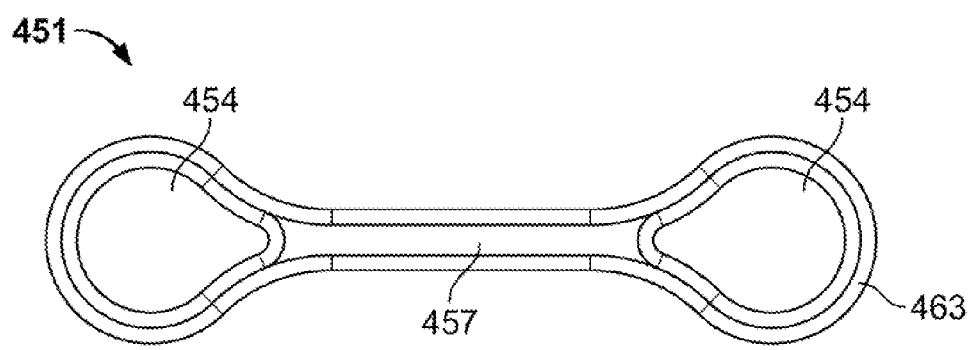
Figure 11C:
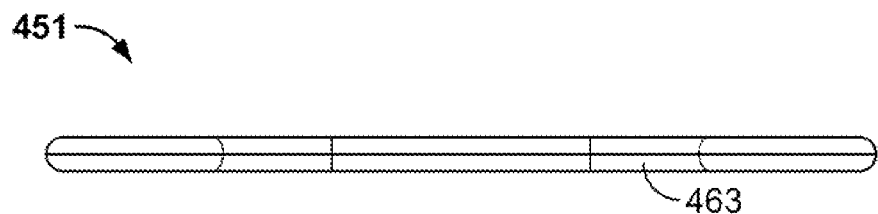

FIGS. 11A to 11C show a perspective view, a top view and a side view of another reinforced pledget embodiment 451. This reinforced pledget embodiment incorporates two openings 454 separated by an axially oriented central link 457 and defining spaces through a support structure 463 through which suture strand free ends 121 are advanced using actuated needles 211 of appendage isolation system 1. The length ("$I_2$") of the central link is chosen based on the distribution requirements. As the flattened profile increases, the length of the central link is increased to accommodate the desire to distribute the forces along a greater length. The openings through the support structure match channel exit point spacing 193 for the grasper.

Figure 12A:
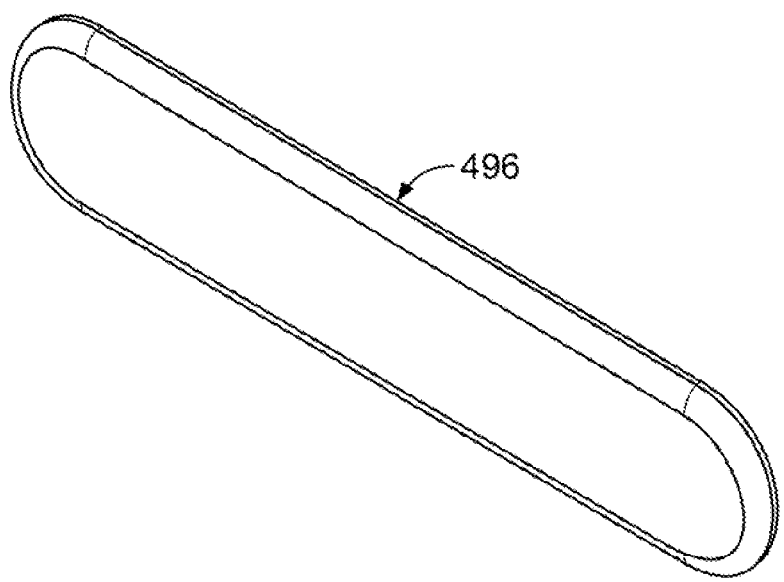
FIGS. 12A to 12C show a perspective view, a top view, and a side view of another reinforced pledget embodiment.
Figure 12B:
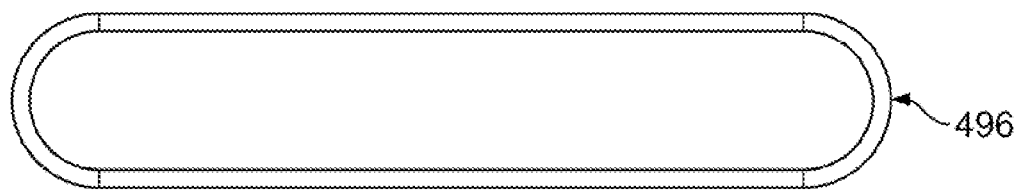
Figure 12C:
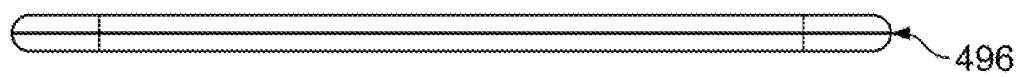
Figure 13A:
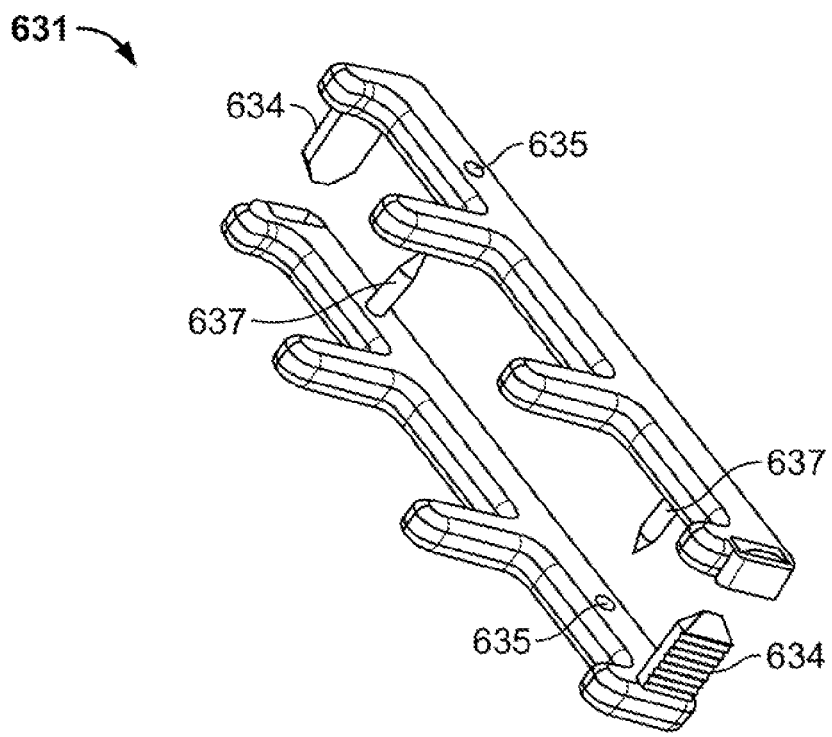
FIGS. 13A to 13C show a perspective view, a top view, and a side view of a penetrating atrial appendage isolation clip embodiment.
Figure 13B:
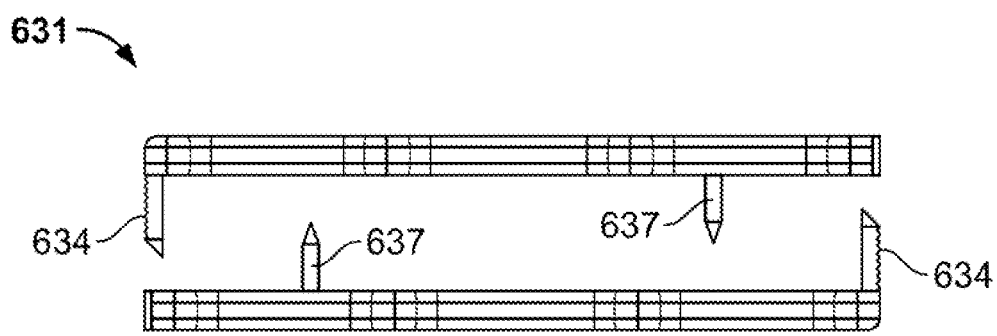
Figure 13C:
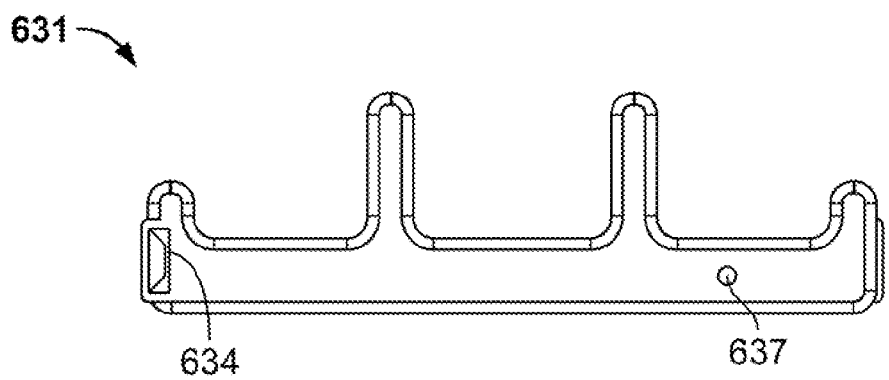
Figure 14A:
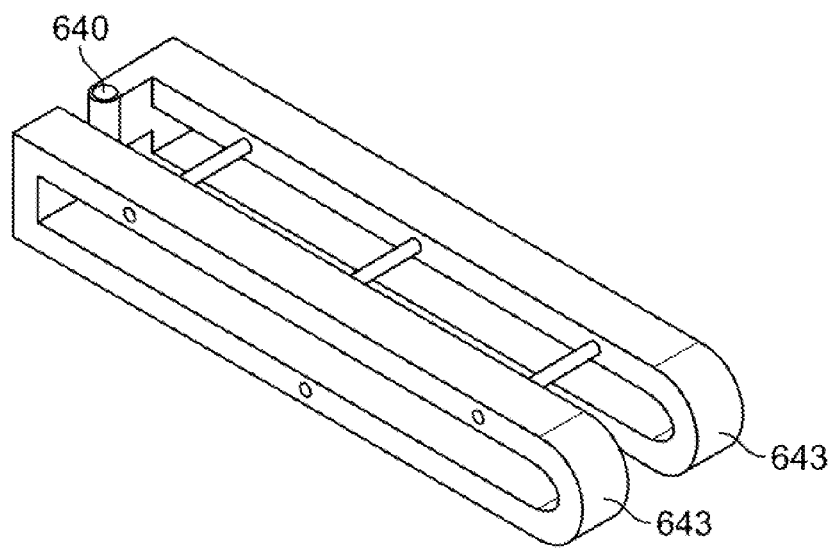
FIGS. 14A to 14C show a perspective view, a top view, and a side view of another penetrating atrial appendage isolation clip embodiment.
Figure 14B:
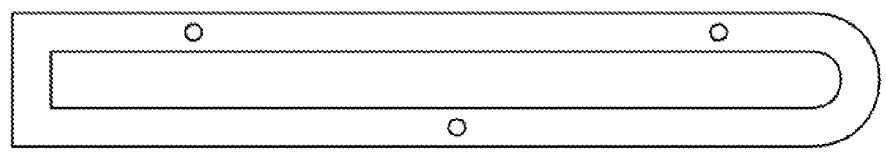
Figure 14C:
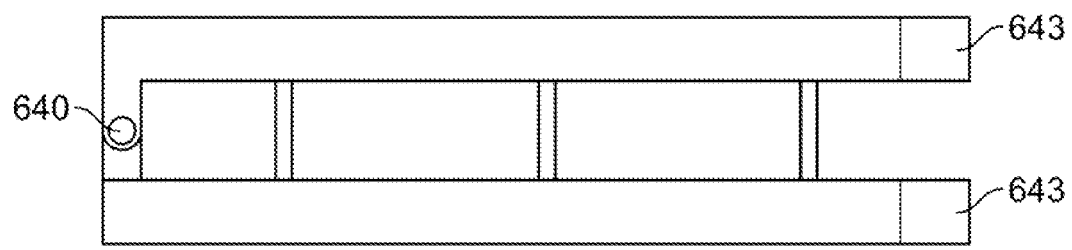

FIGS. 12A to 12C show a perspective view, a top view and a side view of a reinforced pledget embodiment 496. This reinforced pledget embodiment is fabricated from a resilient polymer through which suture strand free ends 121 can be advanced using actuated needles 211 of appendage isolation system 1.

Appendage isolation device embodiments 1 described above can be capable of creating other complex knots that compress opposing soft tissue structures in an atraumatic and consistent fashion during appendage isolation, gastric reduction, lung reduction or resection, or other application involving bringing opposing soft tissue surfaces together to invoke a physiologic response. By coordinating the movements of one or more needles 211, these appendage isolation device embodiments can place at least one suture strand 118 through soft tissue such that the path the suture strand(s) follows through the soft tissue produces a complex knot once the suture strand(s) can be tied. For example, a figure eight knot can be created by passing a single suture strand through eyelets of two puncturing components and passing the components through soft tissue such that they can be angled inward relative to each other and cause the suture strand ends to crisscross once they are advanced or retracted through soft tissue. Once positioned, the free ends of the suture strand can be pulled from the eyelet and tied together thereby producing a figure eight knot. This same device can further be used to pass the free ends of the positioned suture strands through the soft tissue another time to further complicate the knot and increase the pull force and reliability of the knot, once tied. Other knots involving one or more passes of suture strands through the soft tissue can be created with the appendage isolation device embodiments of the invention (involving one or more malleable or resilient needles) by enabling passing the suture strands any number of times and at any position through the soft tissue.

FIGS. 13A to 13C and FIGS. 14A to 14C show perspective views, top views, and side views of penetrating clips 631 capable of isolating atrial appendages 97 or 139 and maintaining the position of the clip relative to the atrial appendage. Each of the two embodiments incorporate locking mechanisms 634 (such as a pair of surfaces as shown that allows movement in a first direction but not in a second), to maintain the clip in a compressed orientation around the atrial appendage. These embodiments incorporate pins 637 to penetrate through the juxtaposed atrial walls to maintain the placement of the appendage isolation clips relative to the atrial appendage. The appendage isolation clips may also have pockets 635 that receive the pins 637 of the opposing or joining clip. Non-penetrating devices have the ability to slip off the atrial appendage. The embodiment in FIGS. 13A to 13C incorporates two locking mechanisms. The embodiment in FIGS. 14A to 14C incorporates a pivot 640 and a single locking mechanism. These clip embodiments can be deployed using a mating clamp that positions the clips relative to the soft tissue structure (e.g. atrial appendage 97 or 139) and upon actuation of the deployment clamp, ends 643 of the clip engage thereby compressing the soft tissue (e.g. atrial appendage) and distributing the compressive forces along the length of the clip.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

Component Material and Processing

Needles or other appendage isolation device components that require the resilience to be deflected into a curved or bent orientation and return to the preformed shape once the deflection force is removed can be fabricated from superelastic or shape memory alloys (e.g. nickel titanium). Superelastic components can elastically deform upon exposure to an external force (e.g. retracting the needle into a confining lumen) and return towards their preformed shape upon reduction or removal of the external force (e.g. advancing beyond the confines of the small diameter lumen, or tubular opening). Superelastic components can exhibit stress-induced martensite characteristics in that they transform from the preshaped austenite form to the more soft and ductile martensite form upon application of stress and transform back toward the more strong and hard austenite form once the stress is released or reduced.

Superelastic components can alternatively exhibit austenite or martensite properties at ambient temperature depending on whether the component needs to demonstrate resilience or malleability, respectively. The composition of the shape memory alloy defines the finish and start martensite transformation temperatures (Mf and Ms) and the start and finish austenite transformation temperatures (As and Af) to accommodate the desired material response. When fabricating shape memory alloys that exhibit stress induced martensite the material composition can be chosen such that the maximum temperature that the material exhibits stress-induced martensite properties (Md) is greater than Af and the range of temperatures between Af and Md can cover the range of ambient temperatures to which the support members are exposed. When fabricating shape memory alloys that exhibit austenite properties and do not transform to martensite in response to stress, the material composition can be chosen such that both Af and Md are less than the range of temperatures to which the supports are exposed. Of course, Af and Md can be chosen at any temperatures provided the shape memory alloy exhibits superelastic properties throughout the temperature range to which they are exposed. Nickel titanium having an atomic ratio of 51.2% Ni and 48.8% Ti exhibits an Af of approximately −20° C.; nickel titanium having an atomic ratio of 50% Ni to 50% Ti exhibits an Af of approximately 100° C. [Melzer A, Pelton A. Superelastic Shape-Memory Technology of Nitinol in Medicine. Min Invas Ther & Allied Technol. 2000: 9(2) 59-60].

Such superelastic materials are able to withstand strain (e.g. 8% strain or greater, depending on the number flexion cycles) without plastically deforming. As such, these superelastic materials can be capable of elastically exerting a force upon deflection. Materials other than superelastic shape memory alloys can be used provided that they can be elastically deformed within the anticipated temperature, stress, and strain parameters. Such materials can include other shape memory alloys, bulk metallic glasses, amorphous Beryllium, suitable ceramic compositions, spring stainless steel 17-7, Elgiloy™, superelastic polymers, etc.

The appendage isolation device components (e.g. needle, stylett, jaws, shaft, pledget support, etc) can be fabricated from at least one rod, wire, band, bar, tube, sheet, ribbon, other raw material having the desired pattern, cross-sectional profile, and dimensions, or a combination of cross-sections. The rod, wire, band, bar, sheet, tube, ribbon, or other raw material can be fabricated by extruding, press-forging, rotary forging, bar rolling, sheet rolling, cold drawing, cold rolling, using multiple cold-working and annealing steps, casting, or otherwise forming into the desired shape. The components can be cut or incorporate cut features by conventional abrasive sawing, water jet cutting, laser cutting, EDM machining, photochemical etching, or other etching techniques.

Components of the appendage isolation device that need to be attached can be bonded by laser welding, adhesively bonding, soldering, spot welding, mechanically engaging, using shrink tubing, or other attachment means. Multiple components can be bonded to produce various subassemblies or components.

For several of the components (e.g. needles), at least one wire, tube, ribbon, sheet, rod, band or bar of raw material is cut to the desired length and thermally formed into the desired 3-dimensional configuration. When thermally forming superelastic components, or features fabricated into superelastic components, the raw material can be stressed into the desired resting configuration using forming fixtures, and the material is heated to 300-600 degrees Celsius for a period of time, typically between 15 seconds and 2 minutes. Once the volume of superelastic material reaches the desired temperature, the superelastic material is quenched by inserting into chilled or room temperature water or other fluid. Multiple thermal forming steps can be utilized to sequentially bend the raw material into a resting shape where the bend or curve exceeds the material limits achieved during a single thermal forming process.

Once the components are fabricated and formed into the desired 3-dimensional geometry, they can be tumbled, sand blasted, bead blasted, chemically etched, ground, mechanically polished, electropolished, or otherwise treated to remove any edges and/or produce a smooth surface.

Coverings for appendage isolation device components (e.g. support structures of the reinforced pledgets) can be fabricated from biocompatible polymer such as expanded PTFE, PEBAX®, polyester, polyurethane, urethane, silicone, polyimide, other thermoplastic, thermoset plastic, or elastomer. The support structure of the reinforced pledgets comprise a metal (e.g. titanium, tantalum, tungsten, etc.), metal alloy (e.g. stainless steel, spring steel, nickel titanium, etc.), or resilient polymer. The support structures may or may not be encapsulated in a covering, such as those listed above. The coverings can be extruded, injection molded, dipped, or applied using another manufacturing process involving embedding the support structure within the covering. The covering can alternatively comprise a bioabsorbable material that is broken down over a period of time leaving the support structure in place. The coating can be encapsulated within the covering or carried by the covering. Such pharmacologic coatings include antiproliferative substances, or agents designed to prevent adhesions, affect thrombosis, inhibit hyperplasia, or promote or discourage platelet congregation around the reinforced pledget.

Such agents may include: rapamycin, dactinomycin, sirolimus, everolimus, Abt-578, tacrolimus, taxanes (such as paclitaxel), pyrolitic carbon, titanium-nitride-oxide, steroids, non-steroidal anti-inflammatories, paclitaxel, fibrinogen, thrombin, phosphorylcholine, heparin, rapamycin, radioactive 188Re and 32P, silver nitrate, camptothecin, etoposide, fluorouracil, vincristine, vinblastine, podophylotoxin, estramustine, noscapine, griseofulvin, and dicoumarol. It is noted that the composition or implant may also include additional substance as required by the location of the implant/pledget/clip/etc. It should be understood that the bio-active substances includes all forms of the substances (e.g., analogs and derivatives, etc.)

Needle components can be fabricated from wire, ribbon, rod, band, bar, or other cross-sectional geometry having a diameter between 0.010" and 0.200". The wire (or other geometry raw material) is flattened along certain sections, cut to define an eyelet, and ground to form a sharpened tip. In this case a beveled tip is illustrated; it should be noted that alternative sharpened tips (e.g. cutting edge, pointed, etc.) can be fabricated.

The methods herein may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art.

The same may hold true with respect to method-based aspects of the invention in terms of additional acts as commonly or logically employed. In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Stated otherwise, except as specifically defined herein, all technical and scientific terms used herein are to be given as broad a commonly understood meaning as possible while maintaining claim validity.

The breadth of the present invention is not to be limited by the examples provided and/or the subject specification, but rather only by the plain meaning (and any definitions provided herein) of the claim terms employed.

We claim:

1. A method for compressing a portion of a patient's heart, the method comprising:

placing a pledget body on an exterior of a first wall of an appendage of the patient's heart, where the appendage comprises at least a second tissue wall, where the first tissue wall and second tissue wall define a cavity where the pledget body comprises a tissue contacting planar surface allowing the pledget body to distribute stress applied to the tissue wall over the entire tissue contacting planar surface of the pledget body;

moving the first and second tissue walls together;

passing a far end of a first suture through the pledget body and the first and second tissue walls; and securing a near end of the first suture such that the end is prevented from passing through the tissue walls, where the tissue contacting planar surface of the pledget body reduces the stress applied by the near end of the first suture on the exterior of the first tissue wall when the first suture is in a state of tension.

2. The method of claim 1, where securing the far end of the first suture comprises a securing technique selected from tying, attaching a locking member, heating, applying an adhesive, and a combination thereof.

3. The method of claim 1, further comprising: placing a secondary pledget body on an exterior of the second wall; and inserting a far end of the first suture through the secondary pledget body and subsequently securing the far end of the first suture such that it is prevented from returning through the tissue walls, where the secondary pledget body reduces the stress applied by the far end of the first suture on the exterior of the second tissue wall when the first suture is in a state of tension.

4. The method of claim 3, where securing the far end of the first suture comprises a securing technique selected from tying, inserting a locking member, heating, applying an adhesive, and a combination thereof.

5. The method of claim 3, where the far end of the first suture is attached to a first needle.

6. The method of claim 5, further comprising inserting a device through a chest wall of the patient, where the device comprises a plurality of jaws configured to move the first and second tissue walls together.

7. The method of claim 6, where the pledget body is removably located on a first jaw for the inserting of the pledget body through the chest wall.

8. The method of claim 7, where the secondary pledget body is removably located on a second jaw for the inserting of the pledget body through the chest wall.

9. The method of claim 6, where the device comprises two opposing jaws.

10. The method of claim 6, further comprising advancing the first needle through at least one channel in the device.

11. The method of claim 10, where the first needle comprises a shape-memory alloy.

12. The method of claim 11, where the shape-memory alloy exhibits pseudo-elastic properties.

13. The method of claim 10, where the first needle comprises a plastically deformable material.

14. The method of claim 10, where the first needle comprises an elastically deformable material.

15. The method of claim 10, where advancing the first needle comprises advancing the first needle through the pledget body after the first needle exits the channel.

16. The method of claim 15, where the pledget body comprises at least one eyelet and where the first needle passes through the eyelet.

17. The method of claim 15, where advancing the needle comprises further advancing the needle through the secondary pledget body.

18. The method of claim 17, where securing the near and far ends of the first suture occurs after further advancing the needle through the secondary pledget body.

19. The method of claim 15, further comprising curving the needle by advancing the needle through a curved channel.

20. The method of claim 10, further comprising a handle mechanism configured to moving the jaws.

21. The method of claim 20, where actuating the handle mechanism causes the first and second tissue walls to move together.

22. The method of claim 21, where actuating the handle mechanism also causes advancement of the first needle at least into the pledget.

23. The method of claim 10, where the near end of the first suture is attached to a second needle.

24. The method of claim 23, where the second needle and the first needle are passed through the tissue walls such that the near and far ends of the first suture cross.

25. The method of claim 3, further comprising inserting a second suture through at least one of the first or secondary pledget.

26. The method of claim 25, further comprising securing the ends of the second suture using a securing technique selected from tying, attaching a locking member, heating, applying an adhesive, and a combination thereof.

27. The method of claim 1, where the pledget body further has a material selected from PTFE, PEBAX, polyester, polyurethane, urethane, silicone, polyimide, a thermoplastic polymer, a thermoset polymer, an elastomer.

28. The method of claim 1, where the pledget body comprises a support structure selected from a metal, a metal alloy, and a polymer.

29. The method of claim 1, where the pledget body comprises a pharmacological substance located on or in the pledget body.

30. The method of claim 29, where the pharmacological substance comprises an agent selected from an antiproliferative agent, an agent to prevent adhesions, an anti-thrombosis agent, an agent that inhibits hyperplasia, an agent that affects platelet congregation.

* * * * *